(12) United States Patent
Lomicka (10) Patent No.: US 9,901,424 B2
(45) Date of Patent: *Feb. 27, 2018

(54) POROUS IMPLANT DEVICE WITH IMPROVED CORE

(71) Applicant: Zimmer Dental, Inc., Carlsbad, CA (US)

(72) Inventor: Matthew J. Lomicka, Littleton, CO (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/259,454

(22) Filed: Sep. 8, 2016

(65) Prior Publication Data

US 2017/0049536 A1 Feb. 23, 2017

Related U.S. Application Data

(63) Continuation of application No. 14/031,608, filed on Sep. 19, 2013, now Pat. No. 9,439,738, which is a continuation of application No. 12/624,608, filed on Nov. 24, 2009, now Pat. No. 8,602,782.

(51) Int. Cl.
*A61C 8/00* (2006.01)
*A61C 8/02* (2006.01)
*A61K 6/04* (2006.01)

(52) U.S. Cl.
CPC .......... *A61C 8/0015* (2013.01); *A61C 8/0006* (2013.01); *A61C 8/006* (2013.01); *A61C 8/0012* (2013.01); *A61C 8/0018* (2013.01); *A61C 8/0022* (2013.01); *A61C 8/0074* (2013.01); *A61K 6/04* (2013.01)

(58) Field of Classification Search
CPC ... A61C 8/0015; A61C 8/0006; A61C 8/0022; A61C 8/006; A61C 8/0074; A61K 6/04
See application file for complete search history.

(56) References Cited

U.S. PATENT DOCUMENTS 2,721,387 A 10/1955 Ashuckian
3,314,420 A 4/1967 Smith et al.
3,423,830 A 1/1968 Halpern et al.
(Continued)

FOREIGN PATENT DOCUMENTS

CA 2506845 A1 7/2004
CN 101505678 A 8/2009
(Continued)

OTHER PUBLICATIONS

"U.S. Appl. No. 12/624,608, Examiner Interview Summary dated Jan. 15, 2013", 3 pgs.
(Continued)

*Primary Examiner* — Heidi M Eide
(74) *Attorney, Agent, or Firm* — Schwegman Lundberg & Woessner, P.A.

(57) ABSTRACT

An implant device has an exterior portion forming an exterior surface of the implant. The exterior portion is made of a porous material defining passages through the exterior portion. An inner portion has an outer surface with a treated area that is accessible from the exterior surface through the passages. The treated area has a treatment for direct attachment to bone or soft tissue.

23 Claims, 4 Drawing Sheets

(56) References Cited

U.S. PATENT DOCUMENTS

| | | |
|---|---|---|
| 3,423,831 A | 1/1969 | Semmelman |
| 3,435,526 A | 2/1969 | Brancato |
| 3,497,953 A | 3/1970 | Weissman |
| 3,685,115 A | 8/1972 | Scott |
| 3,713,860 A | 1/1973 | Auskern |
| 3,740,851 A | 6/1973 | Weissman |
| 3,797,113 A | 3/1974 | Brainin |
| 3,849,887 A | 11/1974 | Brainin |
| 3,896,547 A | 4/1975 | Kulwiec |
| 3,905,109 A | 6/1975 | Cohen et al. |
| 3,896,457 A | 7/1975 | Yamanishi et al. |
| 3,906,550 A | 9/1975 | Rostoker et al. |
| 3,919,773 A | 11/1975 | Freeman |
| 3,934,347 A | 1/1976 | Lash et al. |
| 3,992,725 A | 11/1976 | Homsy |
| 4,011,602 A | 3/1977 | Rybicki et al. |
| 4,016,651 A | 4/1977 | Kawahara et al. |
| 4,086,701 A | 5/1978 | Kawahara et al. |
| 4,097,935 A | 7/1978 | Jarcho |
| 4,122,605 A | 10/1978 | Hirabayashi et al. |
| 4,131,597 A | 12/1978 | Bluethgen et al. |
| 4,178,686 A | 12/1979 | Riess et al. |
| 4,195,366 A | 4/1980 | Jarcho et al. |
| 4,199,864 A | 4/1980 | Ashman |
| 4,229,170 A | 10/1980 | Perez |
| 4,244,689 A | 1/1981 | Ashman |
| 4,252,525 A | 2/1981 | Child |
| 4,259,072 A | 3/1981 | Hirabayashi |
| 4,281,991 A | 8/1981 | Michi et al. |
| 4,321,042 A | 3/1982 | Scheicher |
| 4,375,967 A | 3/1983 | Schaefer |
| 4,379,694 A | 4/1983 | Reiss |
| 4,381,918 A | 5/1983 | Ehrnford |
| 4,411,624 A | 10/1983 | Ogino et al. |
| 4,431,420 A | 2/1984 | Adair |
| 4,439,152 A | 3/1984 | Small |
| 4,448,758 A | 5/1984 | Nagai et al. |
| 4,475,892 A | 10/1984 | Faunce |
| 4,478,904 A | 10/1984 | Ducheyne et al. |
| 4,483,678 A | 11/1984 | Nishio et al. |
| 4,492,577 A | 1/1985 | Farris et al. |
| 4,531,915 A | 7/1985 | Tatum, Jr. |
| 4,531,916 A | 7/1985 | Scantelbury et al. |
| 4,536,158 A | 8/1985 | Bruins et al. |
| 4,548,959 A | 10/1985 | Nagai et al. |
| 4,556,534 A | 12/1985 | Burnett et al. |
| 4,708,652 A | 11/1987 | Fujiu et al. |
| 4,713,006 A | 12/1987 | Hakamatsuka et al. |
| 4,722,688 A | 2/1988 | Lonca |
| 4,731,085 A | 3/1988 | Koch |
| 4,737,411 A | 4/1988 | Graves et al. |
| 4,743,260 A | 5/1988 | Burton |
| 4,744,757 A | 5/1988 | Adair et al. |
| 4,744,759 A | 5/1988 | Bowen |
| 4,820,157 A | 4/1989 | Salvo |
| 4,842,517 A | 6/1989 | Kawahara et al. |
| 4,871,384 A | 10/1989 | Kasuga |
| 4,872,839 A | 10/1989 | Branjnovic |
| 4,872,840 A * | 10/1989 | Bori ............ A61C 3/16 433/173 |
| 4,877,400 A | 10/1989 | Holsclaw |
| 4,880,610 A | 11/1989 | Constantz |
| 4,906,190 A | 3/1990 | Michna |
| 4,909,738 A | 3/1990 | Ai et al. |
| 4,957,554 A | 9/1990 | Mathers et al. |
| 4,957,819 A | 9/1990 | Kawahara et al. |
| 4,960,733 A | 10/1990 | Kasuga et al. |
| 4,969,817 A | 11/1990 | Hiranuma et al. |
| 4,969,913 A | 11/1990 | Ojima |
| 4,983,182 A | 1/1991 | Kijima et al. |
| 5,000,685 A | 3/1991 | Brajnovic |
| 5,002,488 A | 3/1991 | Homsy |
| 5,004,421 A | 4/1991 | Lazarof |
| 5,007,835 A | 4/1991 | Valen |
| 5,009,709 A | 4/1991 | Ibsen et al. |
| 5,049,074 A * | 9/1991 | Otani ............ A61C 8/0012 433/173 |
| 5,055,497 A | 10/1991 | Okada et al. |
| 5,061,285 A | 10/1991 | Koch |
| 5,062,798 A | 11/1991 | Tsuge et al. |
| 5,064,731 A | 11/1991 | Miyazaki et al. |
| 5,076,789 A | 12/1991 | Tanaka |
| 5,087,200 A | 2/1992 | Branjovic et al. |
| 5,120,340 A | 6/1992 | Ducheyne et al. |
| 5,123,844 A | 6/1992 | Wakai et al. |
| 5,125,839 A | 6/1992 | Ingber et al. |
| 5,125,971 A | 6/1992 | Nonami et al. |
| 5,139,424 A | 8/1992 | Yli-Urpo |
| 5,152,687 A | 10/1992 | Amino |
| 5,176,747 A | 1/1993 | Panzera et al. |
| 5,180,303 A | 1/1993 | Hornburg et al. |
| 5,186,626 A | 2/1993 | Tanaka |
| 5,192,325 A | 3/1993 | Kijima et al. |
| 5,194,000 A | 3/1993 | Dury |
| 5,194,001 A | 3/1993 | Salvo |
| 5,199,873 A | 4/1993 | Schulte et al. |
| 5,205,745 A | 4/1993 | Kamiya et al. |
| 5,232,365 A | 8/1993 | Ikehara |
| 5,232,878 A | 8/1993 | Kasuga et al. |
| 5,236,458 A | 8/1993 | Ducheyne et al. |
| 5,238,405 A | 8/1993 | Marlin |
| 5,254,005 A | 10/1993 | Zuest |
| 5,282,861 A | 2/1994 | Kaplan |
| 5,282,863 A | 2/1994 | Burton |
| 5,288,232 A | 2/1994 | Panzera et al. |
| 5,306,673 A | 4/1994 | Hermansson et al. |
| 5,308,391 A | 5/1994 | Komma et al. |
| 5,310,343 A | 5/1994 | Hasegawa et al. |
| 5,312,254 A | 5/1994 | Rosenlicht |
| 5,314,334 A | 5/1994 | Panzera et al. |
| 5,316,476 A | 5/1994 | Krauser |
| 5,342,201 A | 8/1994 | Oden |
| 5,344,318 A | 9/1994 | Wilson et al. |
| 5,344,457 A | 9/1994 | Pilliar et al. |
| 5,346,397 A | 9/1994 | Braiman |
| 5,415,546 A | 5/1995 | Cox, Sr. |
| 5,419,702 A | 5/1995 | Beaty et al. |
| 5,425,639 A | 6/1995 | Anders |
| 5,425,640 A | 6/1995 | Scharf |
| 5,439,380 A | 8/1995 | Marlin |
| 5,443,515 A | 8/1995 | Cohen et al. |
| 5,449,291 A | 9/1995 | Lueschen et al. |
| 5,458,488 A | 10/1995 | Chalifoux |
| 5,468,544 A | 11/1995 | Marcolongo et al. |
| 5,470,230 A | 11/1995 | Daftary et al. |
| 5,476,383 A | 12/1995 | Beaty et al. |
| 5,549,123 A | 8/1996 | Okuyama et al. |
| 5,554,665 A | 9/1996 | Tateosian et al. |
| 5,562,733 A | 10/1996 | Weissbach et al. |
| 5,571,016 A | 11/1996 | Ingber et al. |
| 5,572,652 A | 11/1996 | Robusto et al. |
| 5,575,652 A | 11/1996 | Gaffar et al. |
| 5,584,693 A | 12/1996 | Nishihara |
| 5,591,030 A | 1/1997 | Thiel et al. |
| 5,612,049 A | 3/1997 | Li et al. |
| 5,614,330 A | 3/1997 | Panzera et al. |
| 5,621,035 A | 4/1997 | Lyles et al. |
| 5,624,262 A | 4/1997 | Yarovesky et al. |
| 5,645,934 A | 7/1997 | Marcolongo et al. |
| 5,674,069 A | 10/1997 | Osorio |
| 5,676,745 A | 10/1997 | Kelly et al. |
| 5,683,249 A | 11/1997 | Ibsen et al. |
| 5,685,714 A | 11/1997 | Beaty et al. |
| 5,695,337 A | 12/1997 | Tyszblat Sadoun |
| 5,697,785 A | 12/1997 | Delahaye |
| 5,697,976 A | 12/1997 | Chesterfield et al. |
| 5,697,997 A | 12/1997 | Aronsson et al. |
| 5,698,019 A | 12/1997 | Frank et al. |
| 5,713,994 A | 2/1998 | Kramer et al. |
| 5,723,007 A | 3/1998 | Engel et al. |
| 5,727,943 A | 3/1998 | Beaty et al. |
| 5,755,809 A | 5/1998 | Cohen et al. |
| 5,759,036 A | 6/1998 | Hinds |
| 5,762,500 A | 6/1998 | Lazarof |

(56) References Cited

U.S. PATENT DOCUMENTS

| | | |
|---|---|---|
| 5,772,438 A | 6/1998 | Deom |
| 5,775,912 A | 7/1998 | Panzera et al. |
| 5,785,524 A | 7/1998 | Wolf |
| 5,833,464 A | 10/1998 | Foser |
| 5,833,463 A | 11/1998 | Hurson |
| 5,839,900 A | 11/1998 | Billet et al. |
| 5,843,348 A | 12/1998 | Giordano |
| 5,849,068 A | 12/1998 | Hofmann et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,947,893 A | 9/1999 | Agrawal et al. |
| 5,951,290 A | 9/1999 | Ardizio et al. |
| 5,951,293 A | 9/1999 | Billet et al. |
| 5,951,295 A | 9/1999 | Lyles et al. |
| 5,961,328 A | 10/1999 | Somborac et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,095,817 A | 8/2000 | Wagner et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,213,775 B1 | 4/2001 | Reipur |
| 6,214,049 B1 | 4/2001 | Gayer et al. |
| 6,214,368 B1 | 4/2001 | Lee et al. |
| 6,224,662 B1 | 5/2001 | Nemeth |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,458 B1 | 1/2002 | Schweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinhoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,916,177 B2 | 7/2005 | Lin et al. |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 6,994,726 B2 | 2/2006 | Lin et al. |
| 7,011,522 B2 | 3/2006 | Panzera et al. |
| 7,291,012 B2 | 11/2007 | Lyren |
| 8,562,348 B2 | 10/2013 | Collins et al. |
| 8,602,782 B2 | 12/2013 | Lomicka |
| 8,899,982 B2 | 12/2014 | Damstra et al. |
| 9,066,771 B2 | 6/2015 | Collins et al. |
| 9,439,738 B2 | 9/2016 | Lomicka |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0113690 A1 | 6/2003 | Hollander et al. |
| 2003/0134925 A1 | 7/2003 | Guzauskas |
| 2003/0148247 A1 | 8/2003 | Sicurelli, Jr. et al. |
| 2004/0024081 A1 | 2/2004 | Trieu et al. |
| 2004/0058299 A1 | 3/2004 | Molin et al. |
| 2004/0064192 A1 | 4/2004 | Bubb |

(56) References Cited

U.S. PATENT DOCUMENTS

| | | |
|---|---|---|
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0014108 A1 | 1/2005 | Wohrle et al. |
| 2005/0023710 A1 | 2/2005 | Brodkin et al. |
| 2005/0028424 A1 | 2/2005 | Poinski |
| 2005/0031704 A1 | 2/2005 | Ahn |
| 2005/0084533 A1 | 4/2005 | Howdle et al. |
| 2005/0084819 A1 | 4/2005 | Sims et al. |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1 | 6/2005 | Justin et al. |
| 2005/0136378 A1* | 6/2005 | Ennajimi ............... A61C 8/005 433/173 |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0075826 A1 | 4/2006 | Roberts et al. |
| 2006/0107292 A1 | 5/2006 | Moon |
| 2007/0015110 A1 | 1/2007 | Zhang et al. |
| 2007/0111165 A1 | 5/2007 | Wallick et al. |
| 2007/0118221 A1 | 5/2007 | Robie et al. |
| 2007/0148621 A1 | 6/2007 | Yakir |
| 2007/0184265 A1 | 8/2007 | Ranganathan et al. |
| 2008/0050699 A1 | 2/2008 | Zhang et al. |
| 2008/0241793 A1 | 10/2008 | Collins et al. |
| 2009/0011384 A1 | 1/2009 | Collins et al. |
| 2009/0036908 A1 | 2/2009 | Zokol et al. |
| 2009/0061387 A1 | 3/2009 | Lomicka et al. |
| 2009/0061388 A1 | 3/2009 | Collins et al. |
| 2009/0061389 A1 | 3/2009 | Lomicka et al. |
| 2009/0098510 A1 | 4/2009 | Zhang |
| 2009/0098511 A1 | 4/2009 | Zhang |
| 2009/0233256 A1* | 9/2009 | Schroering ............ A61C 8/0022 433/174 |
| 2010/0003638 A1 | 1/2010 | Collins et al. |
| 2010/0003639 A1 | 1/2010 | Salvi et al. |
| 2010/0003640 A1 | 1/2010 | Damstra et al. |
| 2010/0114314 A1 | 5/2010 | Lomicka et al. |
| 2014/0017633 A1 | 1/2014 | Lomicka |

FOREIGN PATENT DOCUMENTS

| | | |
|---|---|---|
| CN | 102596095 A | 7/2012 |
| DE | 4209569 A1 | 11/1994 |
| DE | 19529036 A1 | 3/1997 |
| DE | 10105398 A1 | 8/2002 |
| EA | 0950421 B1 | 10/1999 |
| EP | 0345584 A2 | 12/1980 |
| EP | 0266313 A2 | 5/1988 |
| EP | 0271236 A1 | 6/1988 |
| EP | 0345581 A2 | 12/1989 |
| EP | 0366018 A1 | 5/1990 |
| EP | 0417018 A1 | 3/1991 |
| EP | 0333503 B1 | 2/1993 |
| EP | 0366018 B1 | 5/1993 |
| EP | 0417018 B1 | 5/1994 |
| EP | 0498923 B1 | 5/1995 |
| EP | 0467948 B1 | 1/1996 |
| EP | 0560279 B1 | 6/2000 |
| EP | 0806211 B1 | 10/2002 |
| EP | 1281372 A1 | 2/2003 |
| EP | 1712205 A2 | 10/2006 |
| EP | 1598028 B1 | 12/2007 |
| FR | 2796265 A1 | 1/2001 |
| GB | 1526780 A | 9/1978 |
| GB | 2401867 B | 11/2004 |
| GB | 2401867 B1 | 10/2005 |
| GB | 2416996 A1 | 2/2006 |
| JP | 61275205 A | 12/1986 |
| JP | 61275205 A2 | 12/1986 |
| JP | 63290559 A | 11/1988 |
| JP | 63290559 A2 | 11/1988 |
| JP | 1025480 A | 1/1989 |
| JP | 1025840 A | 1/1989 |
| JP | 1025849 A | 1/1989 |
| JP | 2002126071 A | 5/2002 |
| WO | WO-8900410 A1 | 1/1989 |
| WO | WO-9011979 A1 | 10/1990 |
| WO | WO-9320773 A1 | 10/1993 |
| WO | WO-9421190 A1 | 9/1994 |
| WO | WO-9528973 A1 | 11/1995 |
| WO | WO-9721393 A1 | 6/1997 |
| WO | WO-9741809 A1 | 11/1997 |
| WO | WO-9830170 A1 | 7/1998 |
| WO | WO-0021455 A1 | 4/2000 |
| WO | WO-0132072 A2 | 5/2001 |
| WO | WO-0107193 A1 | 11/2001 |
| WO | WO-0187193 A1 | 11/2001 |
| WO | WO-0234155 A1 | 5/2002 |
| WO | WO-0236039 A1 | 5/2002 |
| WO | WO-02062901 A1 | 8/2002 |
| WO | WO-02064100 A1 | 8/2002 |
| WO | WO-03065939 A1 | 8/2003 |
| WO | WO-03065996 A2 | 8/2003 |
| WO | WO-03078508 A1 | 9/2003 |
| WO | WO-03094774 A1 | 11/2003 |
| WO | WO-04054464 A2 | 7/2004 |
| WO | WO-2006107292 A1 | 10/2006 |
| WO | WO 2007/027794 * 3/2007 ............... A61C 8/00 |
| WO | WO-2010002663 A1 | 1/2010 |
| WO | WO-2010106241 A2 | 9/2010 |

OTHER PUBLICATIONS

"U.S. Appl. No. 12/624,608, Final Office Action dated Oct. 25, 2011", 12 pgs.

"U.S. Appl. No. 12/624,608, Non Final Office Action dated May 9, 2011", 12 pgs.

"U.S. Appl. No. 12/624,608, Non Final Office Action dated Nov. 19, 2012", 14 pgs.

"U.S. Appl. No. 12/624,608, Notice of Allowance dated Jun. 4, 2013", 10 pgs.

"U.S. Appl. No. 12/624,608, Response filed Jan. 25, 2012 to Final Office Action dated Oct. 25, 2011", 16 pgs.

"U.S. Appl. No. 12/624,608, Response filed Apr. 19, 2013 to Non Final Office Action dated Nov. 19, 2012", 17 pgs.

"U.S. Appl. No. 12/624,608, Response filed Apr. 25, 2011 to Restriction Requirement dated Apr. 8, 2011", 2 pgs.

"U.S. Appl. No. 12/624,608, Response filed Aug. 9, 2011 to Non Final Office Action dated May 9, 2011", 14 pgs.

"U.S. Appl. No. 12/624,608, Restriction Requirement dated Apr. 8, 2011", 8 pgs.

"U.S. Appl. No. 14/031,608, Advisory Action dated Nov. 25, 2015", 3 pgs.

"U.S. Appl. No. 14/031,608, Final Office Action dated Sep. 17, 2015", 12 pgs.

"U.S. Appl. No. 14/031,608, Non Final Office Action dated Jan. 13, 2016", 25 pgs.

"U.S. Appl. No. 14/031,608, Non Final Office Action dated Apr. 2, 2015", 13 pgs.

"U.S. Appl. No. 14/031,608, Notice of Allowance dated Apr. 29, 2016", 5 pgs.

"U.S. Appl. No. 14/031,608, Preliminary Amendment dated Nov. 15, 2013", 7 pgs.

"U.S. Appl. No. 14/031,608, Response filed Mar. 31, 2016 to Non-Final Office Action dated Jan. 13, 2016", 8 pgs.

"U.S. Appl. No. 14/031,608, Response filed Jun. 23, 2015 to Non Final Office Action dated Apr. 2, 2015", 13 pgs.

(56) References Cited

OTHER PUBLICATIONS

"U.S. Appl. No. 14/031,608, Response filed Nov. 10, 2015 to Final Office Action dated Sep. 17, 2015", 12 pgs.
"Canadian Application Serial No. 2,773,224, Office Action dated Oct. 21, 2015", 3 pgs.
"Chinese Application Serial No. 201080050015.9, Office Action dated Jul. 2, 2014", w/English Translation, 19 pgs.
"Chinese Application Serial No. 201080050015.9, Response filed Nov. 17, 2014 to Office Action dated Jul. 2, 2014", w/English Claims, 12 pgs.
"Flocculants, Binders, and Bonds", Chapter 11, Molecular Binders, (1995), 173-177.
"International Application Serial No. PCT/US2006/020130, International Search Report dated Feb. 6, 2007", 7 pgs.
"International Application Serial No. PCT/US2006/033893, International Search Report dated Jan. 29, 2007", 1 pg.
"International Application Serial No. PCT/US2007/069562, International Search Report dated Jul. 7, 2008", 4 pgs.
"International Application Serial No. PCT/US2008/074616, International Search Report dated Dec. 16, 2008", 4 pgs.
"International Application Serial No. PCT/US2008/074642, International Search Report dated Feb. 12, 2009", 4 pgs.
"International Application Serial No. PCT/US2008/074645, International Search Report dated Dec. 29, 2008", 9 pgs.
"International Application Serial No. PCT/US2008/074655, International Search Report dated Feb. 18, 2009", 9 pgs.
"International Application Serial No. PCT/US2009/048456, International Search Report dated Apr. 27, 2010", 5 pgs.
"International Application Serial No. PCT/US2009/048469, International Search Report and Written Opinion dated Oct. 19, 2009", 9 pgs.
"International Application Serial No. PCT/US2009/048476, International Search Report dated Dec. 10, 2009", 13 pgs.
"International Application Serial No. PCT/US2009/048481, International Search Report dated Dec. 10, 2009", 13 pgs.
"International Application Serial No. PCT/US2009/062308, International Search Report dated Jan. 21, 2010", 9 pgs.
"International Application Serial No. PCT/US2010/055975, International Preliminary Report on Patentability dated May 30, 2012", 7 pgs.
"International Application Serial No. PCT/US2010/055975, International Search Report dated Mar. 17, 2011", 4 pgs.
"International Application Serial No. PCT/US2010/055975, Written Opinion dated Mar. 17, 2011", 6 pgs.
"Japanese Application Serial No. 2012-539941, Notice of Reasons for Rejection dated Jun. 2, 2015", English Translation, 4 pgs.
"Japanese Application Serial No. 2012-539941, Office Action dated Apr. 30, 2014", w/English Translation, 10 pgs.
"Japanese Application Serial No. 2012-539941, Response filed Oct. 23, 2014", w/English Claims, 12 pgs.
"PEEK-CLASSIX", Information Sheet Invibio Ltd., Properties of PEEK-CLASSIX White Granular, (Nov. 2003), 2 pgs.
"Two Applications of Transmucosal Milled Ceramic in Implantology", Preliminary Clinical Examples; Implant Quintessence International vol. 27, Issue 8, (1996), 533-548.
Barclay, C W, et al., "The clinical assessment of a ceramic-coated transmucosal dental implant collar", International Journal of Prosthodont. 1996—vol. 9, Issue 5, [Online]. Retrieved from the internet <URL:http://www.ncbi.nlm.nih.gov/pubmed/9108748>, (Oct. 1996), 466-472.
Cass, Richard B, et al., "Innovative Ceramic-Fiber Technology Energizes Advanced Cerametrics", The American Ceramic Society, American Ceramic Society Bulletin, (Nov. 2003), 9701-9706.
Ganz, Scott D, "Presurgical Planning With CT-Derived Fabrication of Surgical Guides", J Oral Maxiofac Surg 63, Suppl 2, (2005), 59-73 pgs.
Kan, Joseph Y K, "Computer-Guided Immediate Provisionalization of Anterior Multiple Adjacent Implants; Surgical and Prosthodontia: Rationale", Practical Procedures & Aethetic Dentistry, vol. 18, No. 10, (2006), 617-623 pgs.
Matinlinna, Jukka P, et al., "An Introduction to Silanes and Their Clinical Applications in Dentistry", The International Journal of Prosthodontics, vol. 17, No. 2, (2004), 155-164.
Reed, James S., "Chapter 24, Injection Molding", Principles of Ceramics Processing, 2nd Edition, New York : Wiley, (1995), 477-481.
Rosenfeld, Alan L, "Prosthetically Directed Implant Placement Using Computer Software to Ensure Precise Placement and Predictable Prosthetic Outcomes. Part 1: Diagnostics, Imaging, and Collaborative Accountability", International Journal of Periodontics & Restorative Dentistry, vol. 26, No. 3, (2006), 215-221.
Zhou, Yan, et al., "Shape Optimization of Randomly Oriented Short Fibers for Bone Cement Reinforcements", Materials Science & Engineering A 393, (2005), 374-381.
"Canadian Application Serial No. 2,773,224, Response filed Apr. 7, 2016 to Office Action dated Oct. 21, 2015", 7 pgs.
"Chinese Application Serial No. 201080050015.9, Office Action dated Dec. 11, 2014", w/English Translation, 10 pgs.
"Chinese Application Serial No. 201080050015.9, Response filed Feb. 25, 2015 to Office Action dated Dec. 11, 2014", w/English Claims, 10 pgs.
"Japanese Application Serial No. 2012-539941, Response filed Nov. 27, 2015 to Office Action dated Jun. 2, 2015", w/English Claims, 11 pgs.

* cited by examiner

POROUS IMPLANT DEVICE WITH IMPROVED CORE

BACKGROUND

Field of the Invention

The present invention relates to porous implants and, in particular, to an implant with a porous material mounted on a core.

Description of the Related Art

Dental implants are commonly used to anchor dental restorations or prosthetic teeth at one or more edentulous sites in a patient's dentition at which the patient's original teeth have been lost or damaged. The dental implant is typically threaded or press-fit into a bore which is drilled into the patient's mandible or maxilla at the edentulous site. Typically, a dental implant device is provided in one or two pieces. For a two piece device, an anchoring member or implant supports a separate coronal dental abutment, which in turn provides an interface between the implant and a dental restoration. For a one piece integral device, the device has an abutment section coronal to an implant section of the device. In either case, the restoration is typically a porcelain crown fashioned according to known methods.

For a two-piece device, there are two-stage surgery implants (also called endosseous implants) that only rise to the crest of the mandible or maxilla. In this case, the surgery is often performed in two stages. In the initial stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. The temporary prosthesis or healing member is removed and replaced with the permanent prosthesis, which is attached to the abutment with cement or with a fastener, for example.

Alternatively, a one-stage surgery, two-piece implant, also called a transgingival implant, is placed in a single stage because it extends through the gingiva for attachment to an abutment. The one-piece implant also is placed in the jaw in a single stage.

Although the osseointegration of existing dental implants into surrounding bone has proven adequate, further improvements in osseointegration of dental implants are desired. For example, patients would prefer the shortest healing time from surgery to the time the implant can be fully impacted by occlusal forces. Also, a desire exists to provide strongly osseointegrated implants for high risk patients, such as smokers, diabetics and/or abnormally slow bone growth.

DETAILED DESCRIPTION

Figure 1:
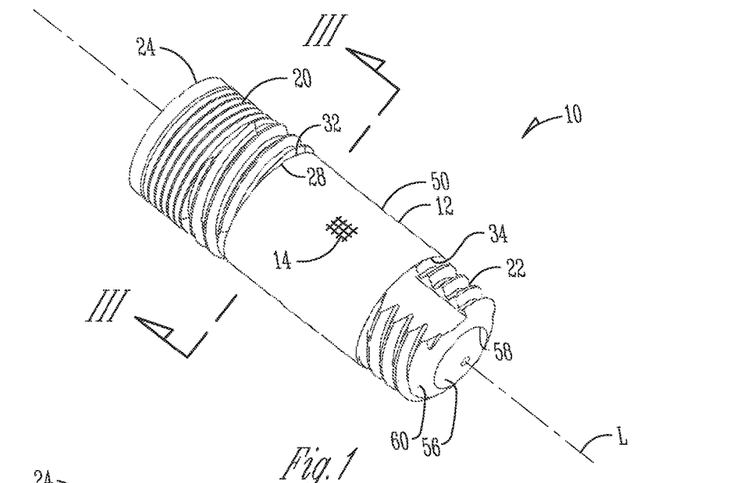
FIG. 1 is a side perspective view of a dental implant device.
Figure 2:
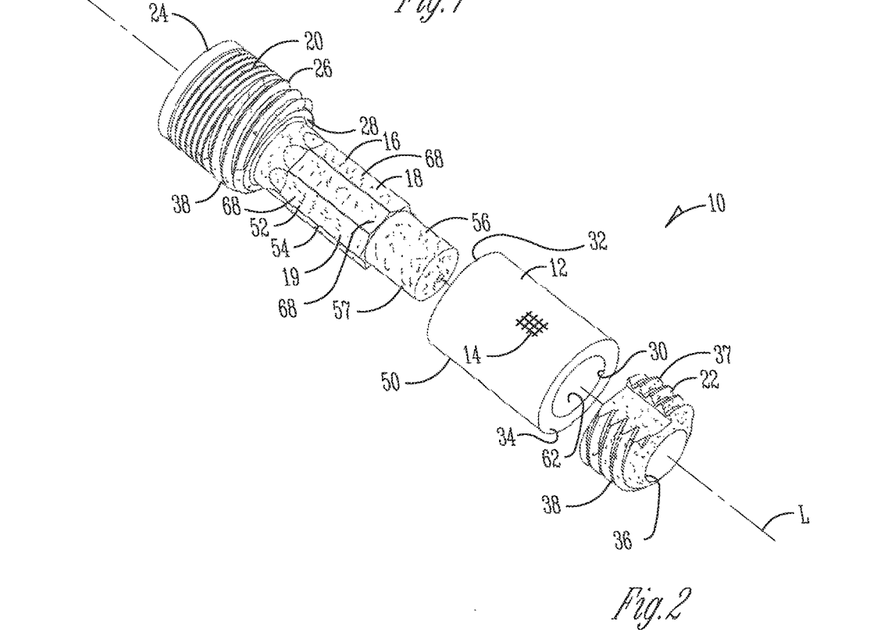
FIG. 2 is an exploded perspective view of the dental implant device of FIG. 1.
Figure 3:
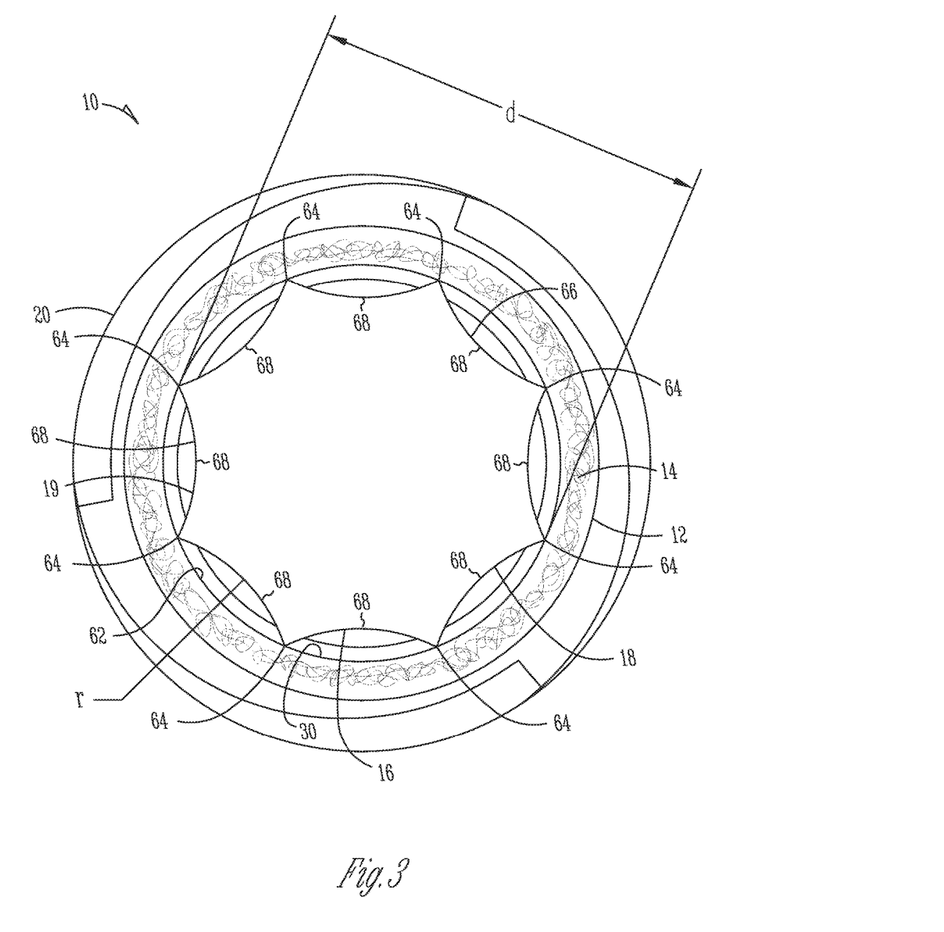
FIG. 3 is a bottom, cross-sectional view of the dental implant device of FIG. 1 taken along the line 3-3 shown on FIG. 1.

Referring to FIGS. 1-3, to improve osseointegration onto the implant, an implant device 10 for placement in bone has an exterior portion 12 made of a porous material 14 that bone can grow into to improve long term stability of the implant device. Such a porous material may also increase short term stability for immediate loading because of its large friction coefficient with surrounding bone as explained in greater detail below. The exterior portion 12 may be placed on or around an interior portion or core 16 that supports the exterior portion and adds strength to the implant device 10. The core 16 may have a surface treatment 18 to further improve osseointegration with bone that has grown through the exterior portion 12 and onto the core 16. Alternatively, or additionally, the core 16 may also have an outer shape or periphery 19 configured to limit rotation of the exterior portion 12 relative to the core 16 for proper placement of the implant 10 in a bore in bone and to increase both long term and short term stability.

Now in more detail, in the illustrated example, the implant 10 is a dental implant for insertion into a mandible or maxilla. The implant 10 is used to anchor one or more dental prostheses, and includes a coronal head portion or head 20. The interior portion or core 16 extends apically from the head 20. In one form, the head 20 and core 16 are integrally formed but may be separate pieces secured to each other by threading, friction fit, welding (laser or e-beam), and so forth. A separate anchor 22 (also referred to as the stem or apical portion) is configured to engage the core 16 so that the head 20 and the anchor 22 cooperatively retain the porous exterior portion 14 therebetween on the implant 10.

For the illustrated example, the coronal end 24 of the head 20 is configured with male or female engagement structure that receives corresponding structure from a separate abutment. It will be appreciated, however, that instead of the two-stage implant 10 shown, the head 20 may have an extended height to extend through gingiva and form a single-stage implant, or may have an integral abutment to form a one-piece implant.

The head 20 has an outer cylindrical or tapering surface 26 that extends to an apical end surface 28. The core 16 has a reduced outer diameter compared to the diameter of the outer surface 26 and extends apically from an apical end surface 28 of head 20 so that apical end surface 28 forms a shoulder to abut and retain exterior portion 12 on the core 16. In one specific form, the exterior portion 12 is a sleeve or collar with a bore 30 that receives the core 16. In one form, the collar 12 has a radial thickness of about 0.03 inches (about 0.75 mm). A coronal end 32 of the exterior portion 12 faces and/or abuts the apical end surface 28. An apical end 34 of the exterior portion 12 faces and/or engages the anchor 22.

The anchor 22 may be secured to an apical end portion 56 of the core 16 to secure the exterior portion 12 between the head 20 and the anchor 22. The anchor 22 may have a bore 36 for receiving the core 16, and the two pieces may then be welded together thereby permanently securing the exterior portion 12 on the core 16. It will be understood that many alternative configurations are contemplated such as the core 16 and anchor 22 being held together by threads or press-fit, or the core 16 being integral to the anchor 22 or entirely separate instead of integral to the head 20 as mentioned above, and as long as the porous exterior portion 12 is maintained adjacent the core 16.

The core 16, head 20, and anchor 22 (whether or not one or more of the pieces are separate or integrally formed) are made of a suitable biocompatible material such as titanium, titanium alloy, stainless steel, zirconium, cobalt-chromium molybdenum alloy, polymers such as polyether ketone ketone (PEKK) for one example, ceramic, and/or composite material.

The outer surfaces 26 and 37 of the head 20 and anchor 22 may have threads 38 for threading the implant 10 into a bore in bone or may be press-fit into the bore instead. Thus, the outer surfaces 26 and 37 may alternatively or additionally have surface treatment for promoting cortical bone and/or cancellous bone growth. The head outer surface 26 may additionally or alternatively be treated to promote an epithelium or soft tissue barrier and/or promote soft tissue growth if the head 20 extends into the gingival layer. In this case, barrier or soft tissue growth treatments can be placed adjacent to soft tissue or the interface between bone and soft tissue. Such treatments may include macro or micro threading, or circumferential or annular grooves, other patterned or random recesses caused by etching (such as acid etching), blasting (such as with sand, with or without HA particles, for example), or also coating of titania (titanium oxide) or other materials that create some adhesion between soft tissues and biomaterials. The surface treatment of outer surfaces 26 and 37 may or may not be the same as the surface treatment of the core 16 described below.

Figure 4:
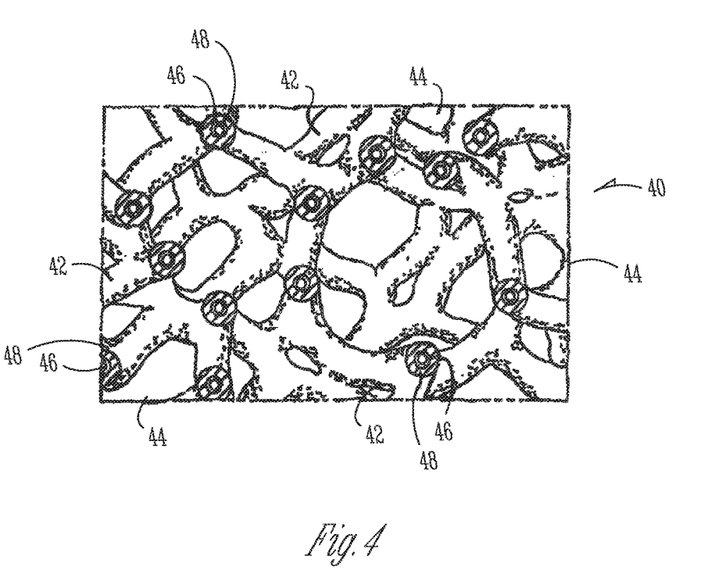
FIG. 4 is a close-up, fragmentary view of a porous material on the dental implant device of FIG. 1.

Referring to FIG. 4, the porous material 14 forming the exterior portion 12 may include metal, and in one form, is a porous tantalum portion 40 which is a highly porous biomaterial useful as a bone substitute and/or cell and tissue receptive material. An example of such a material is produced using Trabecular Metal™ technology generally available from Zimmer, Inc. of Warsaw, Ind. Trabecular Metal™ is a trademark of Zimmer Technology, Inc. Such material may be formed from a reticulated vitreous carbon foam substrate which is infiltrated and coated with a biocompatible metal, such as tantalum, etc., by a chemical vapor deposition ("CVD") process in a manner disclosed in detail in U.S. Pat. No. 5,282,861, the disclosure of which is fully incorporated herein by reference. Other metals such as niobium, or alloys of tantalum and niobium with one another or with other metals may also be used.

As shown in FIG. 4, porous tantalum structure 40 includes a large plurality of interconnected members, ligaments, or beams 42 defining open spaces 44 there between, with each member 42 generally including a carbon core 46 covered by a thin film of metal 48 such as tantalum, for example. The open spaces or passages 44 between members 42 form a matrix of continuous channels having no dead ends, such that growth of cancellous bone entirely through porous tantalum structure 40 is uninhibited. In other words, the bone can grow from an exterior surface 50 of the implant 10 formed by the exterior portion 12, generally radially through the passages 44 of the exterior portion 12, and onto the core 16.

The porous tantalum may include up to 75%-85% or more of voids therein. Thus, porous tantalum is a lightweight, strong porous structure which is substantially uniform and consistent in composition, and closely resembles the structure of natural cancellous bone, thereby providing a matrix into which cancellous bone may grow to anchor implant 10 into the surrounding bone of a patient's jaw which increases stability. The rough exterior surface of such porous metal part 12 has a relatively high friction coefficient with adjacent bone forming the bore that receives the implant 10 to further increase initial stability as alluded to above. This structure can produce superior aesthetic results by restricting movement of the implant. These implants can be placed without supplementary surgical procedures, such as bone grafting, and can be placed in areas where traditional implants have been less successful, such as with reduced or decayed alveolar sections, or with patients that have abnormally slow or reduced bone growth.

More specifically, the high level of friction between the porous material and the bone provides immediate stability post surgery. The tantalum struts that extend from the surface of the material create a rasping action that may stimulate bone growth and anchor the implant at the time of placement. The extremely biocompatible tantalum metal that the porous material is made from allows bone to directly oppose the material. The tantalum forms a porous scaffolding that allows bone to grow into the material providing a rapid osseointegration response that quickly augments the initial mechanical fixation to secure the implant. The implant with in-grown bone may have stability greater than a comparably sized implant with only on-grown bone. Finally, the composite of in-grown bone and such a porous material has elastic properties much closer to bone than a solid metal implant, creating a loading environment that is conducive to maintaining bone near the implant.

Regarding the initial stability, as an implant with the porous material is inserted into the bore or cavity in bone, the porous material will bite into the bone by grating, chipping and/or flaking bone pieces off of the bone sidewalls against which the implant device is being placed. When the implant is inserted into the bore or cavity, this "rasping" action may form slight recesses or indents within the sidewall. This may restrict rotational or twisting motion of the implant device within the bore or cavity since the implant device does not have the clearance to rotate out of the indents and within the bore.

The rasping action also accelerates osseointegration onto the implant device and into the pores of the porous material due to the bone compaction into the pores. First, the grating of the bone structure causes the bone to bleed which stimulates bone growth by instigating production of beneficial cells such as osteoblasts and osteoclasts. Second, the bone pieces that fall into the pores on the porous material assist with bone remodeling. In the process of bone remodeling, osteoblast cells use the bone pieces as scaffolding and create new bone material around the bone pieces. Meanwhile osteoclast cells remove the bone pieces through resorption by breaking down bone and releasing minerals, such as calcium, from the bone pieces and back into the blood stream. The osteoblast cells will continue to replace the grated bone pieces from the pores and around the implant device with new and healthy bone within and surrounding the extraction site. Thus, the porous material has increased resistance to twisting or rotation, allows for immediate or very early loading, and increases long-term stability due to the improved osseointegration. Such an implant with ingrown bone has stability greater than a comparably sized implant with only on-grown bone. For instance, loads that typically require a 16 mm long implant may be adequately impacted by an 8 mm long implant. These advantages may be realized no matter the form of the porous implant.

Porous tantalum structure 40 may be made in a variety of densities in order to selectively tailor the structure for particular applications. In particular, the porous tantalum may be fabricated to virtually any desired porosity and pore size, whether uniform or varying, and can thus be matched with the surrounding natural bone in order to provide an improved matrix for bone in-growth and mineralization. This includes a gradation of pore size on a single implant such that pores are larger on an apical end to match cancellous bone, and smaller on a coronal end to match cortical bone, or even to receive soft tissue ingrowth. Also, the porous tantalum could be made denser with fewer pores in areas of high mechanical stress. Instead of smaller pores in the tantalum, this can also be accomplished by filling all, or some of the pores with a solid material.

To provide additional initial mechanical strength and stability to the porous structure, the porous structure may be infiltrated with a filler material such as a non-resorbable polymer or a resorbable polymer. Examples of non-resorbable polymers for infiltration of the porous structure may include a polyaryl ether ketone (PAEK) such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers may include polylactic co-glycolic acid (PLGA), polylactic acid (PLA), polyglycolic acid (PGA), polyhydroxybutyrate (PHB), and polyhydroxyvalerate (PHV), and copolymers thereof, polycaprolactone, polyanhydrides, and polyorthoesters. By providing additional initial mechanical strength and stability with a resorbable filler material, a titanium reinforcing implant core may not be required through the entire length of the porous material. The resorbable material would resorb as the bone grows in and replaces it, which maintains the strength and stability of the implant.

Figures 5, 6:
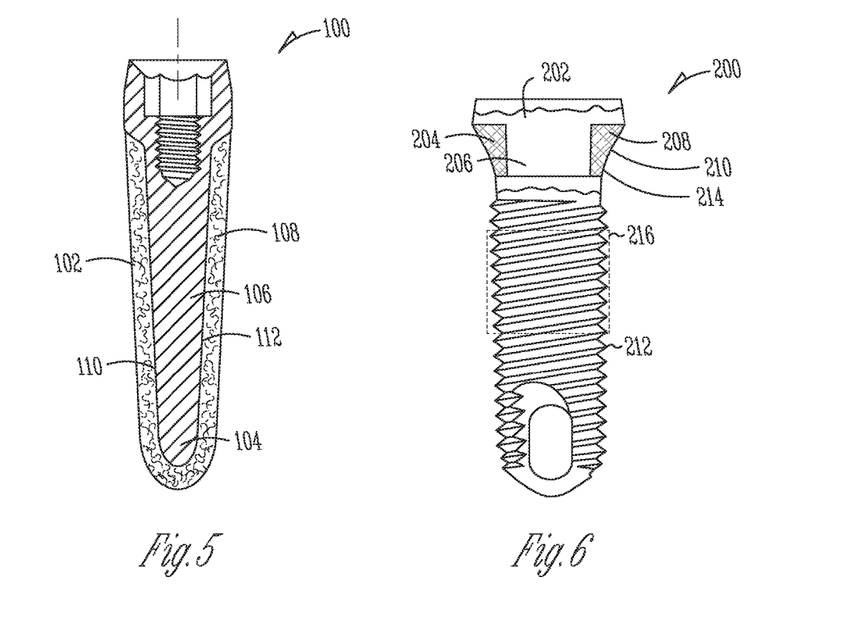
FIG. 5 is a side, cross-sectional view of an alternative dental implant device.
FIG. 6 is a side, partially cross-sectional view of yet another alternative dental implant device.
Figure 7:
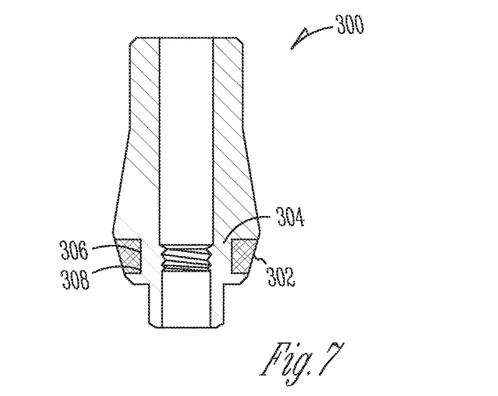
FIG. 7 is a side, cross-sectional view of a further alternative dental implant device.

Referring again to FIG. 1, the surface treatment 18 is applied to a treated area 54 on an outer surface 52 of the interior portion or core 16 for direct attachment to bone. Such strong attachment of the core 16 to bone increases stability. Alternatively, or additionally, the type of surface treatment may be selected to promote an epithelium barrier, soft tissue barrier, or soft tissue growth when a core on the implant is extending through the gingiva as explained below for implants 200 and 300 (FIGS. 6-7).

The treated area 54 is covered by the exterior portion 12 so that the treated area 54 is accessible for direct contact with bone that grows generally radially through the exterior portion 12. In one form, the treated area 54 aligns or corresponds to the exterior portion 12 such that the treated area 54 only extends underneath the exterior portion 12 and does not extend beyond the exterior portion 12 where it is uncovered. In this case, the surface area and outer periphery of the treated area 54 are the same or about the same as that of the exterior portion 12. By another approach, the treated area 54 may be disposed on locations on the core 16 that is not directly covered by the exterior portion 12. For example, the treated area 54 may cover the entire core 16 while the exterior portion 12 only extends in a coronal-apical direction over a part of the core 16. Otherwise, the treated area 54 may have a smaller surface area than that of the exterior portion 12 so that it only extends under the exterior portion 12 whether or not the periphery of the treated area 54 is the same shape as the outer periphery of the exterior portion 12. At a minimum, treated area 54 has at least some part extending underneath the exterior portion 12 and accessible from the exterior surface 50 of the implant 10 through the passages 44.

It will be appreciated that instead of a sleeve or collar, the exterior portion 12 may only form part of the circumference of the implant 10, or may only be located on one or more sides of the implant 10. In that case, the treated area 54 of the core 16 may or may not be configured to align only with the area covered by the exterior portion 12.

In one form, the treated area 54 is at least roughened. This may be performed by gritblasting or sandblasting the treated area 54 to create a random pattern of pits on the outer surface 52 of the core 16 with an average roughness (Ra) of about 20 to 50 μm. The blasting may be performed by spraying Hydroxyapatite (HA) or other bio-compatible materials. By one approach, the treated area 54 has only been treated with sandblasting but alternatively could have a variety of different treatments instead of, or in addition to, the sandblasting. This includes acid etching of the treated area 54 to create random or patterned roughening.

In another example of a treatment 18, the treated area 54 may have at least one coating of a bio-compatible material. The coating may include a bio-reactive material such as HA, collagen, peptides, or other growth factors to promote bone growth onto the core 16 (and/or promote soft tissue growth if the core extends through gingiva). The coating could alternatively or additionally be anti-bacterial and include transition metal ions such as Ag, Cu, or Zn, other bactericidel polymers, antibiotics and/or nanoscale roughness to prevent bacterial colonization on the treated area 54. Other coatings may be applied to form a porosity into the coating for better attachment. This may include Cancellous Structure Titanium (CSTi) provided by Zimmer, Inc. that includes Titanium powder sintered to the core 16 which forms pores through the coating and a roughness to provide improved fixation to the bone or soft tissue. The treated area 54 may alternatively, or additionally, have other roughening treatments such as a circumferentially oriented roughness like threads or annular grooves, or other patterns of roughness (whether on a macro, micro, or nano scale) as long as it intentionally relates to direct attachment to bone (or soft tissue when the core extends near or into the gingiva).

Typically an implant is treated with sandblasting and so forth after the implant is fully assembled so that treatment to exposed areas of an implant can take place in a single step. In this case, however, since the outer surface 52 of the core 16 is treated and then covered, the pieces of implant 10 are treated separately before assembly. Thus, first the head 20 with the core 16, the porous exterior portion 12, and the anchor 22 are shaped as described above. The head 20 and, in turn, the core 16 are then sandblasted or otherwise treated as described above for direct engagement with bone or soft tissue. The head 20 and core 16 are treated separately from the anchor 22, before the exterior portion 12 is mounted on the core 16, and before the head 20 is attached to the anchor 22.

In one form, the entire head 20 including the apical end portion 56 of the core 16 are blasted. It will be appreciated, however, that the core 16 could be the only area treated or blasted while the rest of the head 20 is masked from the treatment. This may be desired if the other exposed areas of the implant 10 receive a different type of treatment that could be damaged by the treatment performed at the core 16, such as coatings, blasting with different particles or particles of different sizes, patterned etching, and so forth. Also, the sidewall 57 of the apical end portion 56 could be masked since it is unexposed within anchor 22 when the implant 10 is assembled, or to provide a smooth connection surface if needed.

Once the treated area 54 is complete, the exterior porous portion 12 is mounted on the core 16, and then the anchor 22 is mounted to the core 16 and secured thereon by laser welding, threading, or other permanent connection. In the illustrated form, after the apical end portion 56 of the core 16 is placed in the bore 36 on the anchor 22, the two are laser welded together along a seam 58 at the apical end portion 60 of the anchor 22. When the head 20 and anchor 22 are laser welded together, the welding process may also undesirably smooth the roughening treatment on the anchor 22 such that sandblasting may need to be reapplied to the anchor 22 on the areas affected by the welding.

In another aspect of implant 10, the core 16 is shaped to limit rotation between the head 20 and the exterior portion 12. If the exterior portion 12 is able to rotate relative to the core 16 and head 20 while the implant 10 is being inserted into a bore in bone, the exterior portion 12 may undesirably bind with the bone (while the head 20 still rotates) so that the implant 10 cannot be properly inserted all the way into the bone bore. Also, better osseointegration occurs when the position of the porous exterior portion 12 in the mouth is not able to change significantly (by rotating on the implant for example) when impacted by occlusal forces thereby maintaining initially fragile bone growth through the exterior portion 12. This results in more long term and short term stability for the implant 10. To accomplish these goals, an anti-rotational connection is formed between the exterior portion 12 and the core 16.

In detail, the implant 10 generally defines a longitudinal axis L while the periphery 19 of the core 16 extends on a cross-section perpendicular to axis L, and the exterior portion 12 has a generally cylindrical wall 62 that defines the bore 30 of the exterior portion 12 and extends around axis L.

The outer surface 52 of the core 16 has at least one generally longitudinally extending groove or flute 68. In the illustrated form, the outer surface 52 forms a circumferential array of the flutes 68 around the core 16. Thus, the flutes 68 form the sides on the periphery 19 providing the periphery 19 with a generally polygonal shape with relatively sharp corners or edges 64 that cut into the wall 62 of the exterior portion 12 when the exterior portion 12 is being inserted axially onto the core 16. The edges 64 are formed relatively sharp by forming each flute 68 with a concave curved surface 66 with a radius r. Thus, in one form, the core 16 has at least two adjoining concave surfaces 66 so that the junction of the two adjoining surfaces 66 form the peak or edge 64 for engaging the collar. This generally secures the edges 64 within the wall 62 of the exterior portion 12 to rotationally secure the collar 12 relative to the core 16.

The radius r of the concave surface 66 is set sufficiently small so that the core 16 retains sufficient mass to have strength to adequately absorb occlusal forces. The radius r is also sufficiently large to provide the peaks 64 with a sharp edge to provide a strong, non-rotational connection between the core 16 and collar 12. In one form, the periphery 19 varies between six and twelve concave sides 66 with a diameter d (from edge to edge) of about 0.060 to 0.230 inches and a radius r from about 0.031 to 0.250 inches depending on the desired size of the implant. In the illustrated form, the eight sides 66 of core 16 have a radius of about 0.0625 inches and an edge to edge diameter of about 0.120 inches. The inner diameter of wall 62 is about 0.114 inches so that each edge 64 cuts into the wall 62 at least about 0.003 inches. Manufacturing tolerances may result in a cut depth of between about 0.002 inches and 0.006 inches. In one form, the edges 64 should cut into the wall 62 at least about 0.002 inches to form a strong anti-rotational engagement.

It will be appreciated that while radius r is the same for all of the sides 66 to maintain a generally uniform cutting depth into the porous exterior portion 12, radius r may be varied as desired instead. This may cause edges that extend farther radially and cut deeper into wall 62 only at certain points around the circumference of the periphery 19 such as two or four opposite sides of the core 16 for a relatively stronger hold.

In an alternative form, the periphery 19 may be other non-circular shapes while the wall 62 remains circular. This creates sections of the core 16 with varying radii that do not have the clearance to rotate relative to the exterior portion 12 and vice-versa. In this case, the periphery 19 may be a flat-sided polygon (whether regular or non-regular) or generally ovaline (such as elliptical, oval, obround, and so forth) or may be some other combination of curved and flat sides. In another alternative, the wall 62 and the periphery 19 have different non-circular shapes to better reduce rotation between the core 16 and the wall 62 such as by having an oval periphery and a hexagonal wall in cross-section as one example. In these cases, an initial rotation of the wall 62 against the periphery 19 fixes the wall 62 against the core 16 by friction or by a portion of the core 16 cutting into the wall 62.

In yet another alternative form, the implant may have the opposite configuration where the outer surface 52 of the core 16 is cylindrical while the wall 62 of the exterior portion 12 is non-circular to form a friction fit between the two.

In a further alternative form, the periphery 19 may have a non-circular shape that corresponds to a non-circular shape of the wall 62 to limit rotation between the two components. For example, the periphery 19 or core 16 may have an outer surface 52 with at least one flat side or portion that coincides with and engages a flat portion of the wall 62 to resist rotation. In one form, both the core 16 and wall 62 may have aligned polygonal cross-sections.

It should also be noted that while the implant 10 may have a generally cylindrical outer surface 50, the implant 10 may also have a morse-type taper so that its diameter decreases as it extends apically to further increase friction with surrounding bone when the implant 10 is pressed or threaded into a bore in the bone. The outer periphery of the implant 10 may also have a non-cylindrical shape to create more friction with a circular bore in the bone.

Referring to FIG. 5, an alternative implant 100 may have a porous exterior portion 102 that covers an apical end 104 of a core 106 to form a pocket 108, and in this example, a tapered generally bullet-shaped pocket 108. In this case, an outer surface 110 of the core 106 has treatment 112 as with treatment 18 explained above for implant 10 for direct attachment to bone (or soft tissue if the core 106 extends adjacent or through the gingiva) that extends entirely through the porous exterior portion 102 via the passages 44 (FIG. 4).

Referring to FIG. 6, other implant forms may be provided for the porous exterior portion and a core on the implant to receive soft tissue in addition to, or rather than, bone. For instance, the implant 200 is a one-stage implant with a transgingival flared end 202 that extends coronally from an endosseous portion 212 of the implant 200. In this case, an exterior portion 204 on the flared end 202 may be in the form of a full or partial ring that is mounted around a core 206. A treatment 210 is applied to the outer surface 208 of the core 206 as with implant 10.

Referring to FIG. 7, in yet another form, the abutment 300 has a porous exterior portion or ring 302 mounted around a core 304 on the abutment to receive soft tissue when the abutment is mounted on a separate two-stage dental implant. The core 302 has an outer surface 306 with a treatment 308 as explained above with implant 10.

By another approach, the treatment areas mentioned herein are zones, and each implant may have a number of zones where each zone has a treatment selected to accomplish a different purpose. In one form, there are at least two distinct zones along the longitudinal axis of the implant, whether the zones are adjacent or spaced from each other. In one case, one or more zones may be placed within bone and its treatment is selected for bone growth, while other zone or zones extend within soft tissue and their treatment is selected for soft tissue growth (or to establish a barrier as mentioned above). The zones in bone may be particularly selected to grow cortical or cancelleous bone. In one form, the implant 10 may have a number of axially spaced partial or full rings for bone growth for example. In the illustrated example, implant 200 may also have one or more zones 214 for soft tissue growth and one or more porous or treated zones 216 (shown in dashed line on FIG. 6) for bone growth. Similarly, abutment 300 may have one or more of the zones and may be supported with an implant that has one or more of the zones.

It will also be understood that the combination of a porous exterior portion intentionally covering a treated area of an interior portion may be used on endosseous implants other than dental implants including implants along the length of a bone, or an implant at joints such as for knees, hips, shoulders, elbows, the spine, and so forth.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental implant comprising:
 a coronal head portion and a non-threaded solid core attached to the coronal head portion, wherein the coronal head portion has a threaded exterior surface configured to engage a wall of a bone tunnel formed in a patient's jaw;
 a porous portion defining a bore that receives the solid core, the solid core being rotationally-locked relative to the porous portion within the bore; and
 an apical anchor portion with an exterior threaded surface configured to engage the wall of the bone tunnel, wherein the apical anchor extends along only an apical section of the dental implant and defines a non-threaded bore that receives the solid core, the solid core being rotationally-locked relative to the apical anchor within its bore, wherein the bore of the porous portion defines a first opening at a first end of the porous portion and a second opening at a second end of the porous portion, and the solid core extends through the first opening and the second opening of the porous portion and into the bore of the apical anchor.

2. The dental implant of claim 1, wherein the solid core is non-circular in shape and is configured to non-rotationally engage the bore of the porous portion.

3. The dental implant of claim 1, wherein the porous portion defines porous passages extending entirely and radially through the porous portion so that bone in-growth can occur through the porous portion and reach the solid core.

4. The dental implant of claim 1, wherein the solid core extends from and forms an integral part of the coronal head portion.

5. The dental implant of claim 1, wherein the solid core comprises a shaft having a maximum diameter that is less than a maximum diameter of a main body of the coronal head portion.

6. The dental implant of claim 1, wherein the porous portion is a porous metal sleeve that surrounds the solid core.

7. The dental implant of claim 1, wherein the coronal head portion includes circumferential groves positioned relatively more coronal of the threaded exterior surface on the coronal head portion.

8. The dental implant of claim 1, wherein the porous portion is positioned between the coronal head portion and the apical anchor, which are both fixed longitudinally relative to the solid core, and the coronal head portion and apical anchor fix the porous portion longitudinally relative to the implant.

9. A method of implanting a dental implant comprising:
 forming a hole in a bone of a patient's mouth, the hole being defined by an internal wall; and
 inserting the dental implant into the hole so that an apical portion and a porous portion of the implant engage the internal wall of the hole in the bone and affix the dental implant within the hole, wherein the implant comprises a coronal head portion and a non-threaded solid core and the porous portion defines a bore that receives the solid core, the solid core being rotationally-locked relative to the porous portion within the bore, and wherein the apical portion comprises an apical anchor extending along only an apical section of the dental implant, the apical anchor comprising a non-threaded bore that receives the solid core, the solid core being rotationally locked relative to the apical anchor within its bore.

10. The method of claim 9, wherein the bore of the porous portion defines a first opening at a first end of the porous portion and a second opening at a second end of the porous portion, and the solid core extends through the first opening and the second opening of the porous portion and into the bore of the apical anchor.

11. The method of claim 10, wherein the porous portion is positioned between the apical anchor and the coronal head portion, both of which are fixed longitudinally relative to the solid core, and the apical anchor and the coronal head portion prevent movement of the porous portion along a longitudinal axis of the implant.

12. The method of claim 10, wherein the apical anchor has an exterior threaded surface, and the method further comprises threading the apical anchor into the hole in the bone so that the exterior threaded surface of the apical anchor engages the internal wall of the hole in the bone.

13. The method of claim 10, further comprising press-fitting the apical anchor into the hole in the bone to affix the implant to the bone.

14. The method of claim 9, wherein the porous portion defines porous passages extending entirely and radially through the porous portion so that bone in-growth can occur through the porous portion and reach the solid core.

15. The method of claim 9, wherein the solid core extends from and forms an integral part of the coronal head portion.

16. The method of claim 9, further comprising attaching an abutment to the coronal head portion and then attaching a dental prosthetic that replicates a natural tooth to the abutment.

17. The method of claim 9, wherein the coronal head portion includes an exterior threaded surface, and the method further comprises threading the coronal head portion into the hole in the bone so that the exterior threaded surface of the coronal head portion engages the internal wall of the hole in the bone.

18. The method of claim 9, wherein the solid core is non-circular in shape and is configured to non-rotationally engage the bore of the porous portion.

19. A method of implanting a dental implant comprising:
    forming a hole in a bone of a patient's mouth, the hole being defined by an internal wall;
    inserting an apical threaded anchor of the dental implant into the hole so that the apical anchor fixably engages the internal wall of the hole in the bone and secures the dental implant in the hole, wherein the apical anchor defines a non-threaded bore and extends along only an apical section of the dental implant;
    inserting a porous portion of the implant into the hole so as to engage the internal wall of the hole in the bone, wherein the porous portion defines a bore; and
    inserting a coronal threaded head portion of the implant into the hole so as to engage the internal wall of the hole in the bone, wherein the implant comprises a non-threaded solid core that is received in the bores of the porous portion and the apical anchor, respectively, wherein the solid core is rotationally-locked relative to the porous portion and the apical anchor within their respective bores.

20. The method of claim 19, wherein the bore of the porous portion defines a first opening at a first end of the porous portion and a second opening at a second end of the porous portion, and the solid core extends through the first opening and the second opening of the porous portion and into the bore of the apical anchor.

21. The method of claim 19, wherein the coronal threaded head portion includes circumferential groves.

22. The method of claim 19, wherein the porous portion is positioned between the apical anchor and the coronal head portion, both of which are fixed longitudinally relative to the solid core, and the apical anchor and the coronal head portion prevent movement of the porous portion along a longitudinal axis of the implant.

23. The method of claim 19, wherein the solid core is non-circular in shape and is configured to non-rotationally engage the bore of the porous portion.

* * * * *